United States Patent
Osawa et al.

(10) Patent No.: US 8,455,241 B2
(45) Date of Patent: Jun. 4, 2013

(54) CULTURE OBSERVATION SYSTEM

(75) Inventors: Shinji Osawa, Funabashi (JP); Tetsuya Miyoshi, Tatebayashi (JP); Tadahisa Saga, Gunma (JP); Ryuzo Tobe, Maebashi (JP); Hiroki Busujima, Ota (JP)

(73) Assignee: Panasonic Healthcare Co., Ltd., Toon-Shi (JP)

( * ) Notice: Subject to any disclaimer, the term of this patent is extended or adjusted under 35 U.S.C. 154(b) by 259 days.

(21) Appl. No.: 12/304,857

(22) PCT Filed: Jun. 12, 2007

(86) PCT No.: PCT/JP2007/061790
§ 371 (c)(1),
(2), (4) Date: Mar. 6, 2009

(87) PCT Pub. No.: WO2007/145198
PCT Pub. Date: Dec. 21, 2007

(65) Prior Publication Data
US 2009/0325280 A1 Dec. 31, 2009

(30) Foreign Application Priority Data
Jun. 16, 2006 (JP) ................. 2006-167725

(51) Int. Cl.
*C12M 1/00* (2006.01)
*C12M 1/34* (2006.01)
*C12M 3/00* (2006.01)

(52) U.S. Cl.
USPC ............... 435/288.7; 435/283.1; 435/287.1; 435/294.1; 435/303.1; 435/289.1

(58) Field of Classification Search
USPC .................. 435/288.7, 283.1–309.4
See application file for complete search history.

(56) References Cited

U.S. PATENT DOCUMENTS 4,629,862 A * 12/1986 Kitagawa et al. ............. 219/200
4,800,164 A * 1/1989 Bisconte .................... 435/286.4

(Continued)

FOREIGN PATENT DOCUMENTS

| JP | 60-137279 | 7/1985 |
|---|---|---|
| JP | 8-285777 | 11/1996 |
| JP | 2004-180675 | 7/2004 |

(Continued)

OTHER PUBLICATIONS

English translation of Japanese Application Publication No, 8-285777A, Nov. 1, 1996.
English translation of Japanese Application Publication No. 2005-323509A, Nov. 24, 2005.

*Primary Examiner* — Nathan Bowers
*Assistant Examiner* — Lydia Edwards
(74) *Attorney, Agent, or Firm* — Kratz, Quintos & Hanson, LLP

(57) ABSTRACT

There is provided a culture observation system by which even a culture other than an observation target culture can be cultured and observation can be properly performed by a microscope during culturing of the culture. A culture observation system S includes a culturing cabinet 2 for forming an environment suitable for culturing cells in a culturing room 13 and an image pick-up device 3 for photographing a microscopic image of the cells. The image pick-up device 3 includes a light source 47 which is provided in the culturing room 13 and a table 37 which is provided in the culturing room 13 to hold the culture as an image pick-up target, and a shelf 7 for accommodating the cells is provided in the culturing room 13 other than the light source 47 and the table 37.

2 Claims, 11 Drawing Sheets

U.S. PATENT DOCUMENTS

| | | | |
|---|---|---|---|
| 5,922,593 A * | 7/1999 | Livingston | 435/288.5 |
| 6,228,636 B1 * | 5/2001 | Yahiro et al. | 435/303.1 |
| 6,597,450 B1 * | 7/2003 | Andrews et al. | 356/317 |
| 6,849,422 B1 * | 2/2005 | Wiles et al. | 435/29 |
| 7,765,868 B2 * | 8/2010 | Pirsch et al. | 73/431 |
| 2005/0051723 A1 * | 3/2005 | Neagle et al. | 250/306 |
| 2005/0282268 A1 * | 12/2005 | Kagayama | 435/288.7 |
| 2006/0141609 A1 * | 6/2006 | Kagayama et al. | 435/287.1 |

FOREIGN PATENT DOCUMENTS

| | | |
|---|---|---|
| JP | 2005-323509 | 11/2005 |
| JP | 2006-11415 | 1/2006 |
| WO | WO 2007/004385 A1 | 1/2007 |

* cited by examiner

CULTURE OBSERVATION SYSTEM

BACKGROUND OF THE INVENTION

The present invention relates to a culture observation system by which a culturing state of a culture can be observed using a microscopic image.

Together with the development in regeneration medicine-related field, the cell culturing using an incubator (culturing means) is increasing. In order to promote the cell culturing, it is required to adjust a culturing space suitable for respective cells, and in the past, incubators performing the temperature control, humidity control and atmosphere control of the culturing space have been developed.

Particularly, when the cell culturing requiring a strict $CO_2$ (carbon dioxide) gas concentration condition as a culturing condition is performed, a $CO_2$ incubator in which $CO_2$ gas concentration in a culturing space can be controlled in addition to a temperature and humidity is used.

Meanwhile, when a culturing state of cells is observed, samples such as the cells cultured in the $CO_2$ incubator are taken out from the incubator to be observed by a phase-contrast microscope, a differential interference microscope, a fluorescence microscope or the like and then the cells are returned to the incubator to be continuously cultured again.

However, when the cells are taken out from the $CO_2$ incubator every observation of the culturing state thereof, culturing conditions for the cells vary and the cells die in some cases. Thus, it is difficult to perform proper culturing. In view of this, a culturing microscope by which cells can be observed while being continuously cultured in a $CO_2$ incubator has been developed (see Japanese Patent Application Laid-Open No. 2006-11415).

In the culturing microscope, an incubator room for culturing the cells is provided integrally with a microscope portion for observing the cells and a tray for mounting sample containers is disposed on a rotation base disposed in the incubator room. The tray has a plurality of sample mounting holes. By controlling the rotation of the rotation base, samples contained in the sample containers can be observed through an objective lens of the microscope.

In addition, an LED for illuminating and a CCD camera are mounted in the microscope room and the light from a sample is incident to the CCD camera via the objective lens, a magnification changing lens and the like. The image photographed by the CCD camera is input to a computer and displayed by a display connected to the computer in real time.

However, as described above, in the culturing microscope, positions for mounting the sample containers are provided on the rotation base in the incubator room for culturing the cells and thus the number of samples which can be cultured (actually, the number of containers containing the sample) is limited.

Accordingly, it is desirable to develop a device by which even a culture which can be cultured with the same conditions as those of a culture such as cells of which a culturing state is observed by a microscope can be cultured by the same device. Meanwhile, in the lower part of the culture microscope, since a microscope room for accommodating a light source is formed in the lower part of the incubator room other than the microscope, a problem occurs in that the size of the device increases by the accommodation amount of the culture.

In addition, when a culture other than an observation target culture is accommodated in the incubator room, the observation target culture is heated to a predetermined temperature by a heater (stage heater) provided in the rotation base, but the other culture, that is, the culture mounted in the incubator room other than the rotation base is heated to the predetermined temperature by a heater for controlling a temperature in the incubator room. These heaters are independently controlled to maintain the predetermined temperature. However, when the temperature on the rotation base is higher than the temperature in the incubator room, dew condensation occurs in the upper part of the sample container mounted on the rotation base and thus a problem occurs in that the culture cannot be observed.

SUMMARY OF THE INVENTION

In view of this, the invention is contrived to solve the conventional technical problem and provides a culture observation system by which even a culture other than an observation target culture can be cultured and observation can be properly performed by a microscope during culturing of the culture.

A culture observation system according to a first aspect of the invention includes a culturing cabinet for forming an environment suitable for culturing a culture in a culturing room and an image pick-up device for photographing a microscopic image of the culture. The image pick-up device includes a light source which is provided in the culturing room and a table which is provided in the culturing room to hold the culture as an image pick-up target, and a shelf for accommodating the culture is provided in the culturing room other than the light source and the table.

A culture observation system according to a second aspect of the invention includes a culturing cabinet for forming an environment suitable for culturing a culture in a culturing room and an image pick-up device for photographing a microscopic image of the culture. The image pick-up device includes a table which is provided in the culturing room to hold the culture as an image pick-up target accommodated in a translucent container. In addition, control means for controlling a temperature in the culturing room and a temperature of the table is provided and controls the temperature of the table to be a value equal to or lower than the temperature in the culturing room and suitable for the culturing the culture.

According to the first aspect of the invention, a culture observation system includes a culturing cabinet for forming an environment suitable for culturing a culture in a culturing room and an image pick-up device for photographing a microscopic image of the culture. The image pick-up device includes a light source which is provided in the culturing room and a table which is provided in the culturing room to hold the culture as an image pick-up target, and a shelf for accommodating the culture is provided in the culturing room other the light source and the table. Thus, even a culture other than the culture as an observation target can be cultured by the same device. Accordingly, an accommodation amount of cultures which can be cultured at one time can be increased.

In addition, without particularly mounting a device for culturing, it is possible to perform only the culturing and perform both of the culturing state observation and the culturing simultaneously and thus convenience can be improved.

According to the second aspect of the invention, a culture observation system includes a culturing cabinet for forming an environment suitable for culturing a culture in a culturing room and an image pick-up device for photographing a microscopic image of the culture. The image pick-up device includes a table which is provided in the culturing room to hold the culture as an image pick-up target accommodated in a transluscent container. In addition, control means for controlling a temperature in the culturing room and a temperature of the table is provided and controls the temperature of the table to be a value equal to or lower than the temperature in the culturing room and suitable for the culturing the culture. Thus, a disadvantage in that dew condensation occurs on an inner surface of the container can be suppressed while the culture accommodated in the container held on the table is cultured.

Accordingly, a disadvantage in that the dew condensation obstructs the culture photographing performed via the container can be avoided and thus proper culture observation can be performed.

DESCRIPTION OF THE PREFERRED EMBODIMENTS

Figure 1:
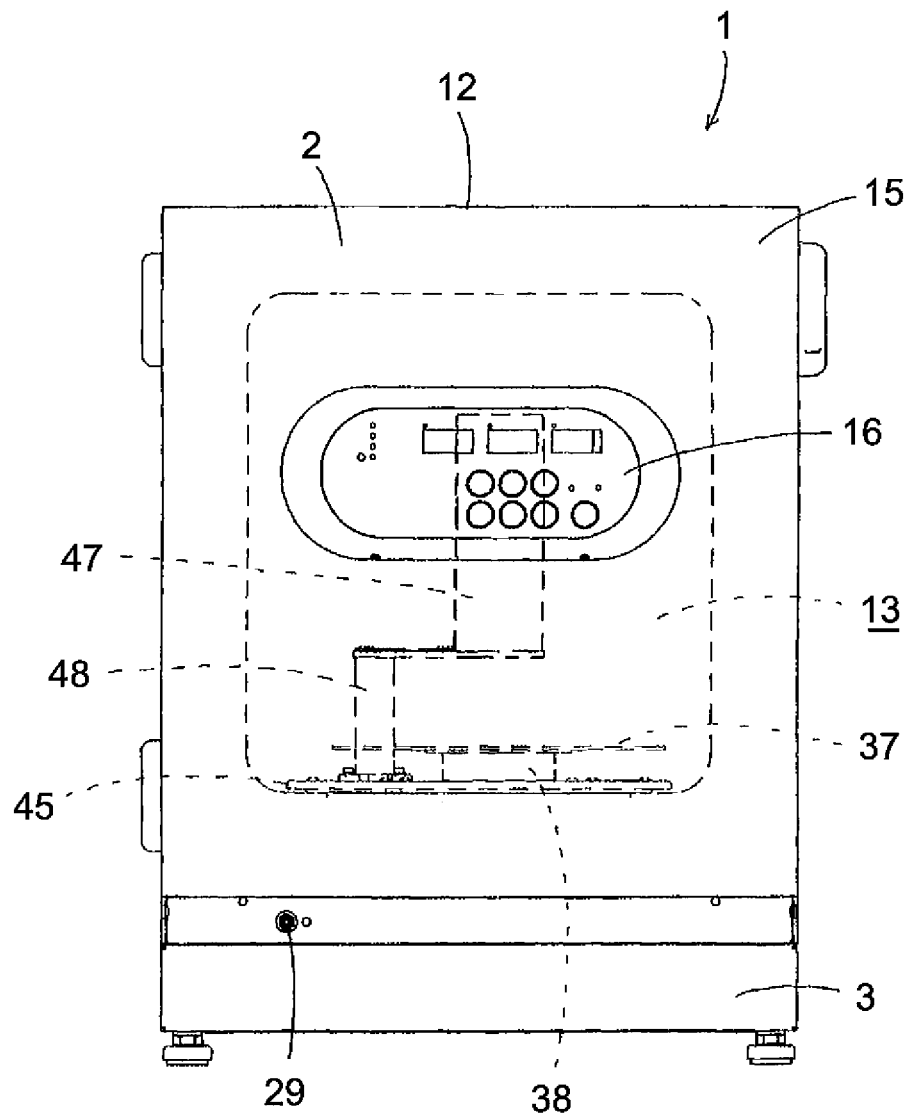
FIG. 1 is a partial perspective front view of a culture observation device of a culture observation system to which the invention is applied.
Figure 2:
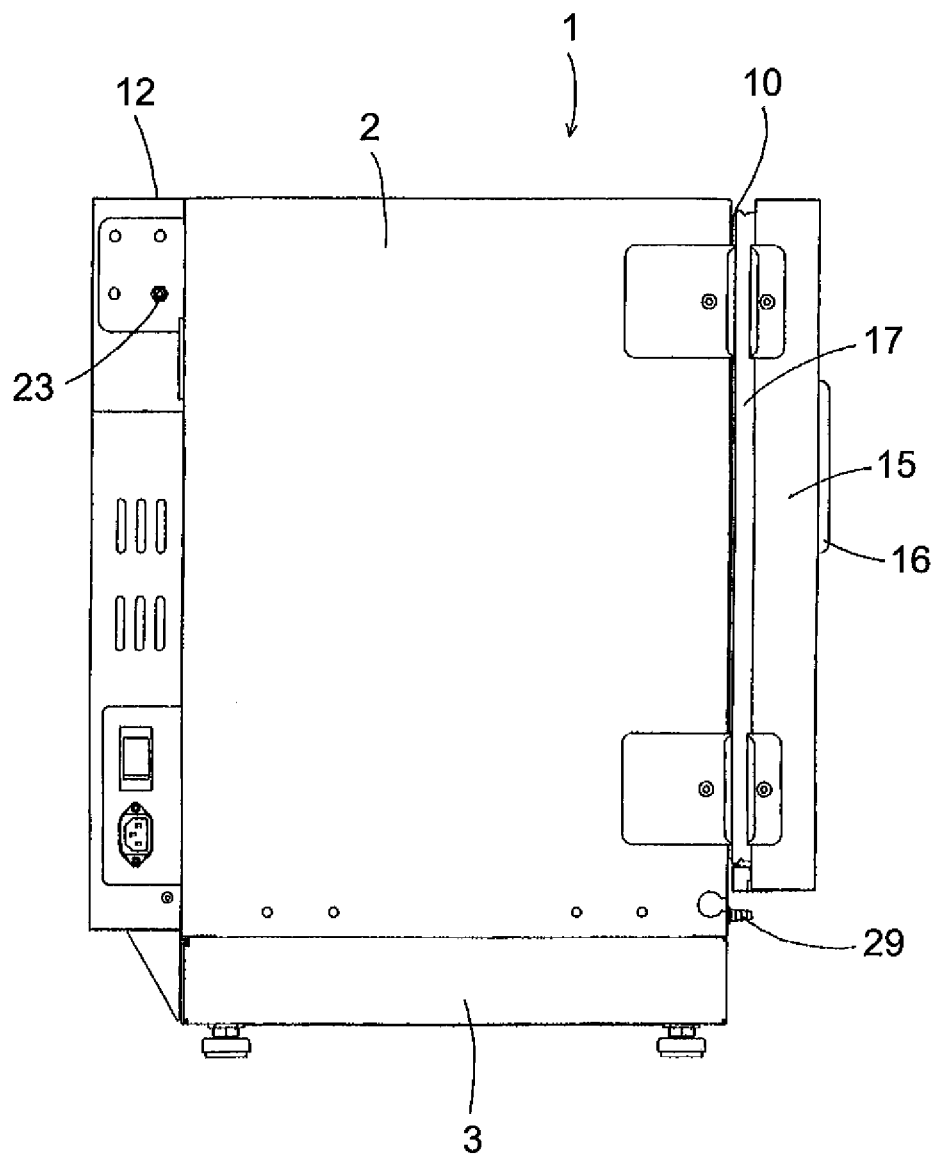
FIG. 2 is a side view of the culture observation device of FIG. 1.
Figure 3:
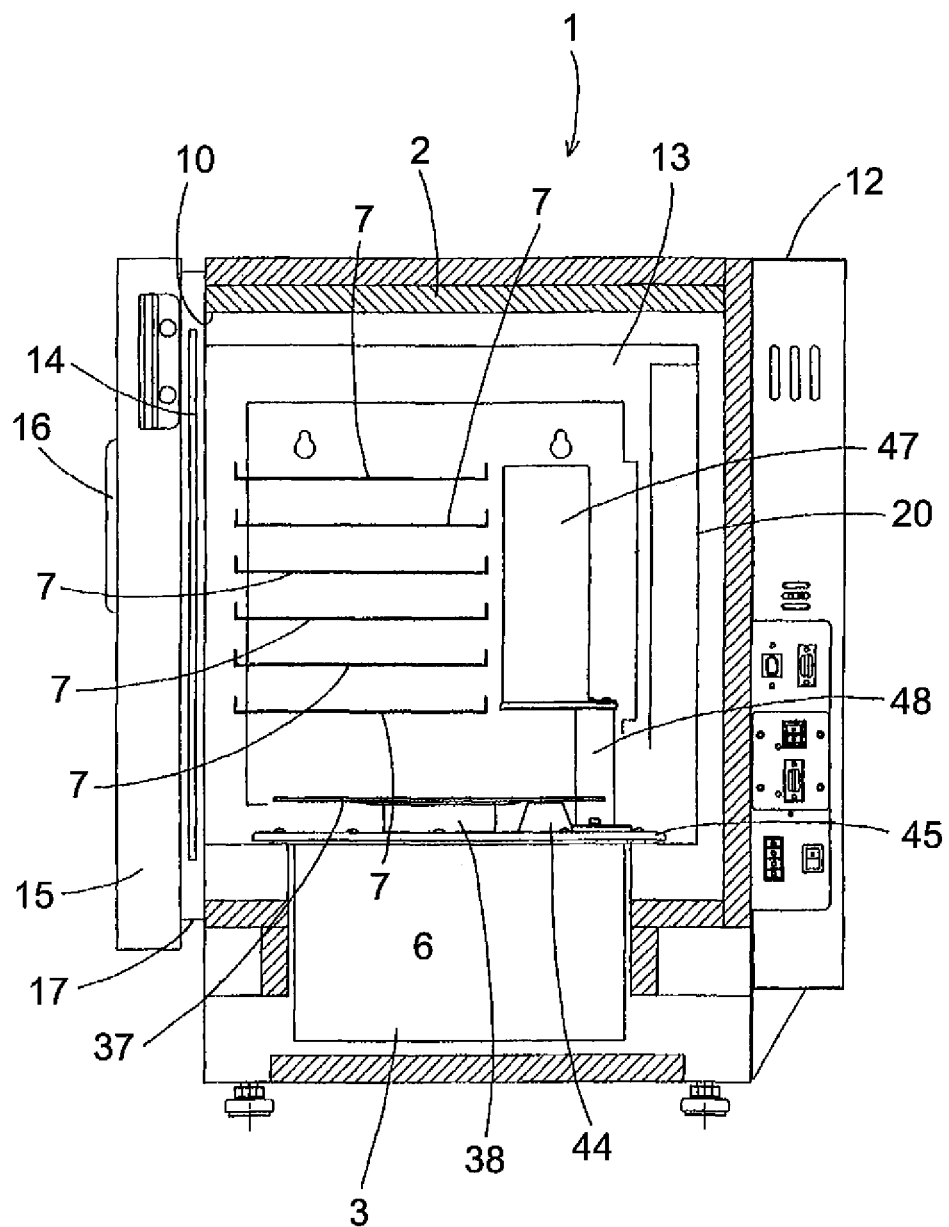
FIG. 3 is a longitudinal sectional side view of the culture observation device of FIG. 1.
Figure 4:
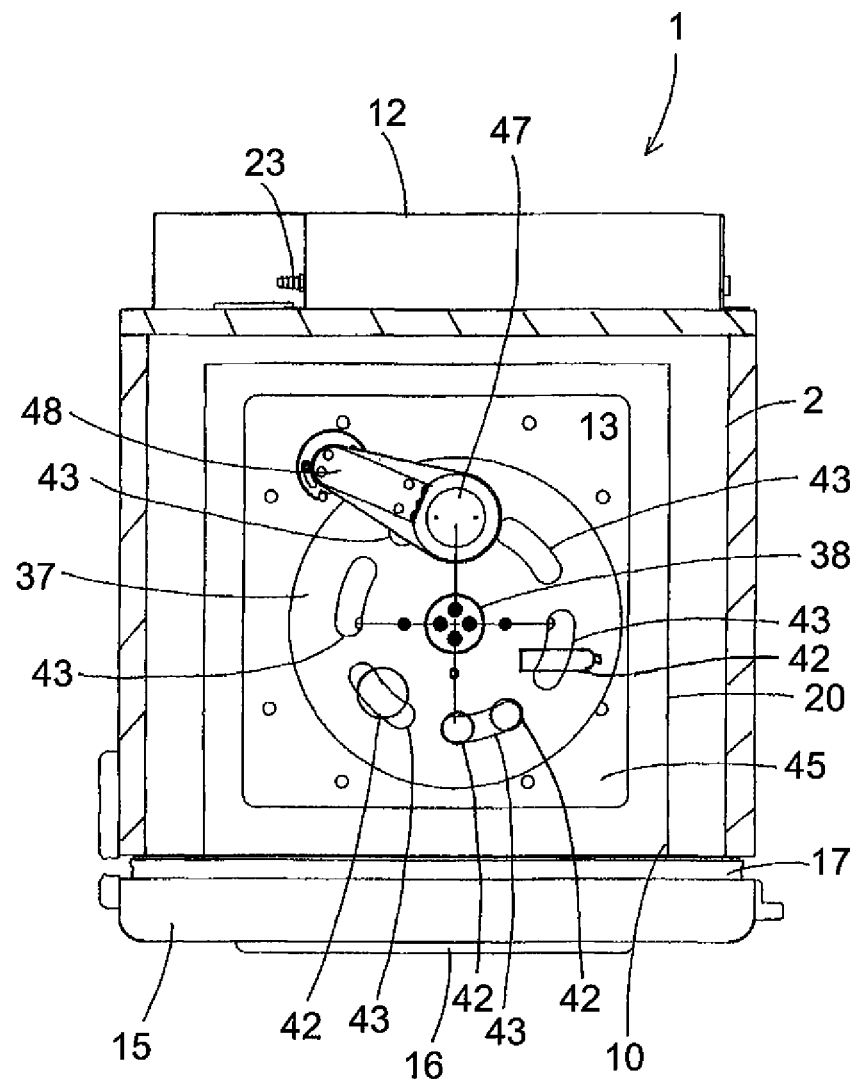
FIG. 4 is a transverse sectional side view of the culture observation device of FIG. 1.
Figure 5:
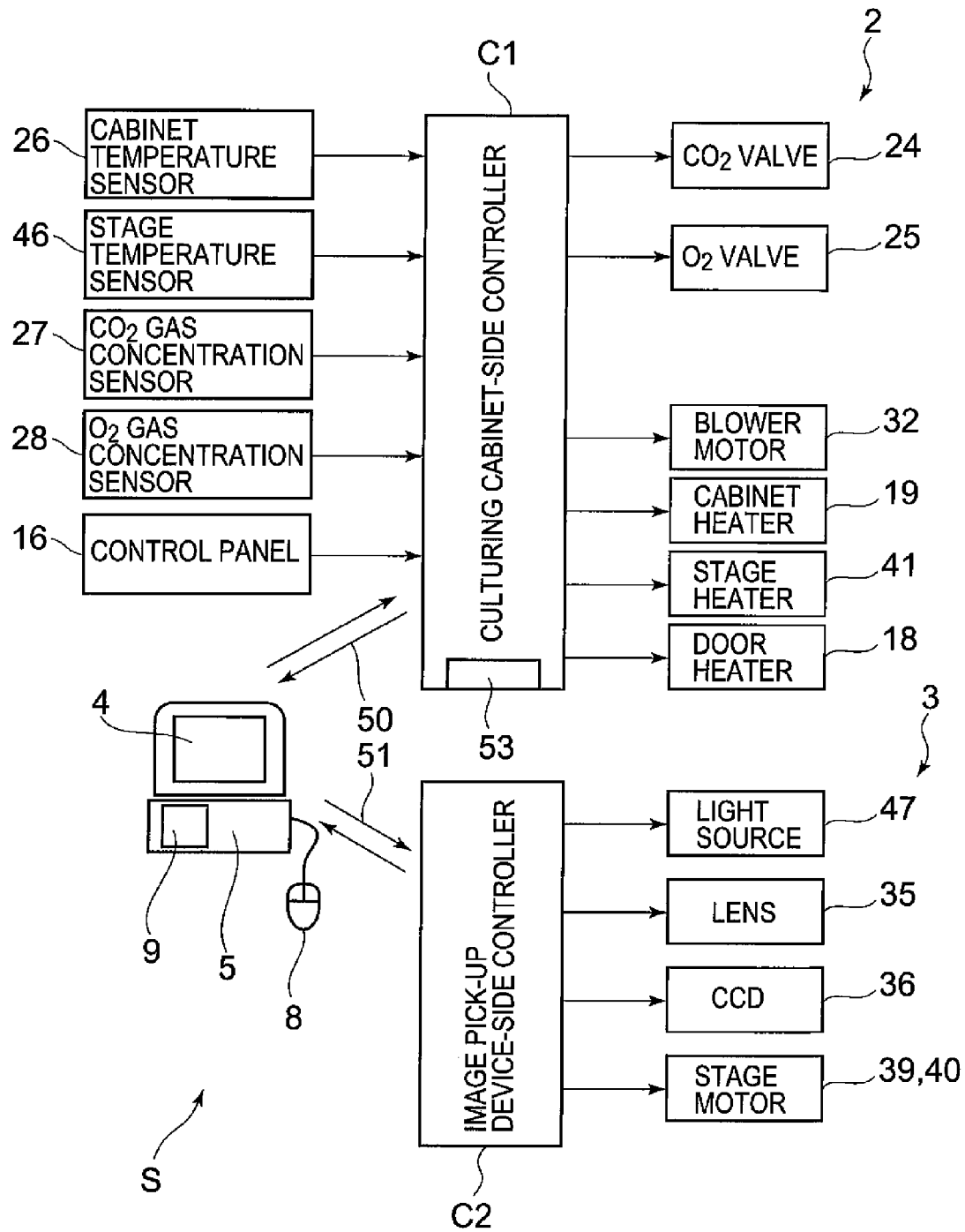
FIG. 5 is an electrical block diagram of a control device of the culture observation system.

Next, an embodiment of the invention will be described in detail with reference to drawings. FIG. 1 is a partial perspective front view of a culture observation device 1 of a culture observation system S to which the invention is applied, FIG. 2 is a side view of the culture observation device 1 of FIG. 1, FIG. 3 is a longitudinal sectional side view of the culture observation device 1 of FIG. 1, FIG. 4 is a transverse sectional side view of the culture observation device 1 of FIG. 1, and FIG. 5 is an electrical block diagram of a control device of the culture observation system S.

The culture observation system S according to this embodiment is a system for a culturing operation of cells as a culture, such as embryonic stem cells which are undifferentiated stem cells (so-called ES cells) present in fertilized eggs, undifferentiated stem cells present in organs which are already formed in the body such as cells to be used in regeneration medicine and the like, including, for example, hematopoietic stem cells, neural tube cells and the like, and fertilized eggs. By the system, a culturing state can be observed while culturing is performed.

The culture observation system S includes a culturing cabinet (culturing means) 2 for forming an environment suitable for culturing cells as a culture (hereinafter, cells will be described as a culture), an image pick-up device (image pick-up means) 3 for photographing a microscopic image of the cells, a display (display means) 4 for displaying the microscopic image photographed by the image pick-up device 3, and a computer 5 as control means for controlling the culturing cabinet 2, the image pick-up device 3 and the display 4. Among them, the culture observation device 1 includes the culturing cabinet 2 and the image pick-up device 3, as shown in FIG. 1. The computer 5 includes a PC including a general-purpose microcomputer, and the like.

A body 12 of the culture observation device 1 is, for example, a heat insulating casing having an opening 10 in one surface (front surface in this embodiment) thereof and a culturing room 13 of the culturing cabinet 2 is formed in the upper part in the body 12 (in the cabinet). In addition, an image pick-up room 6 provided with the image pick-up device 3 is formed in the lower part in the body 12 which is positioned below the culturing room 13.

The body 12 is provided with an openable internal door 14 for closing the opening 10 and a heat insulating door 15 positioned outside the internal door 14. The internal door 14 is formed of a transparent glass plate or the like through which the inside can be viewed, and the inside of the culturing room 13 can be viewed in a state in which the heat insulating door 15 is opened and the internal door 14 is closed. The heat insulating door 15 is provided with a control panel 16 in a front surface thereof and a gasket 17 is attached to an outer circumferential edge of a back surface of the heat insulating door 15 so as to be positioned outside an end surface of the internal door 14. In this manner, the culturing room 13 can be sealed from the outside.

Inner wall surfaces of the body 12 of the culturing room 13 are provided with thermal conductive partition walls 20 with a predetermined interval therebetween. The partition walls 20 are positioned in all the surfaces constituting the culturing room 13, that is, a top surface, a bottom surface, left and right side surfaces, and a rear surface, and a cabinet heater 19 (shown only in FIG. 5) is disposed between the partition wall 20 and the inner wall surface of the body 12. Since the image pick-up device 3 is disposed below the culturing room 13, in the bottom surface of the culturing room 13, the cabinet heater 19 is disposed in a part excluding a part in which the image pick-up device 3 is provided. Further, the back surface of the heat insulating door 15 constituting the front surface of the culturing room 13 in a state in which the door 15 is closed is also provided with a door heater 18 (shown only in FIG. 5). Accordingly, the culturing room 13 can be indirectly heated from all the 6 surfaces via the partition walls 20 and the internal door 14.

On the partition walls 20 constituting the left and right side walls of the culturing room 13, a plurality of shelf installation portions (not shown in the drawings) protruding inward are formed in a plurality of steps, and on the shelf installation portions, a plurality of thermal conductive shelf boards (shelves) 7 having a plurality of communication holes formed thereon are removably installed in a plurality of steps. Further, in this embodiment, since a light source 47 is disposed in the rear part in the culturing room 13 as described later in detail, rear ends of the shelf boards 7 can be installed so as to be disposed in front of a front surface of the light source 47. However, this embodiment is not limited thereto. They can extend up to a position close to the rear surface of the culturing room 13, and a position corresponding to the light source 47 may have a shape (cutout portion having a U-shaped cross-section) to avoid the light source 47.

Meanwhile, the body 12 is provided with a gas supply port 23 so as to communicate with the inside of the culturing room 13 and a gas supply tube (not shown in the drawings) is connected to the gas supply port 23. The gas supply tube is connected to a $CO_2$ gas canister ($CO_2$ gas supply means) via a $CO_2$ gas electromagnetic valve 24 and connected to an $O_2$ gas canister ($O_2$ gas supply means) via an $O_2$ gas electromagnetic valve 25. In the gas canisters, gas higher than a predetermined level in purity is included. The electromagnetic valves 24 and 25 are controlled to be opened and closed by a culturing cabinet-side controller C1 to be described later in detail. The gas supply tube may be provided with humidity adjustment means to supply gas having a predetermined $CO_2$ concentration, $O_2$ concentration, and humidity to the culturing room 13. Moreover, in this embodiment, both $CO_2$ gas and $O_2$ gas can be supplied. However, only the $CO_2$ gas may be supplied.

In addition, in the body 12, a cabinet temperature sensor 26 for detecting an air temperature of the culturing room 13, a $CO_2$ gas concentration sensor 27 for detecting $CO_2$ gas concentration of the culturing room 13, and an $O_2$ gas concentration sensor 28 for detecting $O_2$ gas concentration of the culturing room 13 are provided. All the sensors 26, 27 and 28 are connected to the culturing cabinet-side controller C1, and on the basis of the detection of the sensors, the cabinet heater 19, the door heater 18, the $CO_2$ gas electromagnetic valve 24, and the $O_2$ gas electromagnetic valve 25 are controlled and a temperature and gas concentration of the culturing environment set as described later in detail are controlled. Further, the body 12 is provided with a discharge port 29 for discharging unnecessary air in the culturing room 13 to discharge the air from the culturing room 13.

In the body 12, a blower (not shown in the drawings) for stirring the air in the culturing room 13 and making the state of the air uniform is provided. The blower is operated by a blower motor 32 and the blower motor 32 is controlled by the culturing cabinet-side controller C1.

In the culturing room 13 formed in the body 12, a table 37 constituting the image pick-up device 3 together with a lens 35 such as a magnification changing lens, a CCD camera 36 and the like disposed in the image pick-up room 6 to be described later in detail is provided. The table 37 is made of a thermal conductive material. In addition, in this embodiment, the table is a plate-shaped member having a substantially planar circular shape as described in FIG. 4. In the table 37, a plurality of holes 43 are formed in a communication manner to mount a plurality of sample containers 42 containing a sample such as cells. In this embodiment, 6 holes 43 are formed at a predetermined interval therebetween and the holes 43 are formed away from the center of the table with a predetermined dimension therebetween.

The sample containers 42 are a container of which at least a bottom surface and an upper surface are translucent. For example, they are made of transparent glass or resin. The incident light from the light source 47 passes through the containers and the contents can be observed by an objective lens 44. In addition, an opening of the sample containers 42 can be closed by a lid member including a filter having air permeability and the humidity and gas concentration in the containers 42 can be maintained so as to be the same as those in the culturing room 13.

A rotation shaft 38 made of a thermal conductive material is attached to the center of the table 37. The rotation shaft 38 is connected to a stage motor 39 (shown only in FIG. 5) for rotation movement, of which one end is disposed in the image pick-up room 6. The rotation shaft can be rotated in a horizontal direction by the driving of the stage motor 39. In addition, the rotation shaft 38 can be moved in one direction, that is, in this embodiment, a back-and-forth direction by a stage motor 40 for linear movement. In this manner, the table 37 can be moved by the rotation movement and linear movement and thus the cells in the sample containers 42 mounted on the table 37 can be moved.

A stage heater 41 is attached to an inner surface of the image pick-up room 6 (in the embodiment, inner surfaces of both side walls and front wall) and thus the thermal conductive table 37 attached to one end of the rotation shaft 38 and positioned directly above the image pick-up room 6 can be heated to a predetermined temperature. Further, a stage temperature sensor 46 for detecting a temperature of the table 37 is attached to the table 37.

By a dividing wall 45, the table 37 is partitioned from the culturing room 13 and the image pick-up room 6 provided with the image pick-up device 3 to provide enclosed structure so that the adjusted air in the culturing room 13 does not enter the image pick-up room 6.

The objective lens 44 disposed below the table 37 protrudes from the image pick-up room 6 via the dividing wall 45. By the objective lens 44, the cells in the sample containers 42 mounted in the holes 43 of the table 37 can be observed, and the objective lens is provided at a position corresponding to a position disposed away from the rotation shaft 38 (center of table) at a predetermined interval, that is, a position at which the hole 43 is formed. At a position opposed to the objective lens 44 (above the objective lens 44), the light source 47 of the image pick-up device 3 is provided in the culturing room 13 positioned in the body 12 via an arm 48.

In this embodiment, the light source 47 uses an LED illumination lamp and extends in a vertical direction in the culturing room 13 to illuminate from the above the cells positioned between the objective lens 44 and an illumination hole of the light source 47. The light source 47 is not limited to the LED illumination lamp and may be, for example, a mercury lamp, optical fibers or the like.

In this embodiment, since the shelf boards 7 . . . in the plurality of steps can be installed in the culturing room 13 disposed above the table 37, the light source 47 is disposed at a position not obstructing the taking in/taking out operation of a culture (cells or the like contained in container), which is performed from the opening 10 of the front surface, that is, in this embodiment, at a position in the rear of the culturing space. The objective lens 44 opposed to the illumination hole of the light source 47 is also provided in the rear of the culturing space.

The magnification changing lens 35 and the CCD camera 36 and the like constituting the image pick-up device 3 together with the objective lens 44, the light source 47 and the table 37 are disposed in the image pick-up room 6 together with the motors 39 and 40 as described above. A detailed description for a pick-up system constituted by the objective lens 44, the magnification changing lens 35, and the CCD camera 36 will be omitted because it has the same structure as conventional structure.

Next, a control system (control means) of the culture observation system S in this embodiment will be described with reference to the electrical block diagram of FIG. 5. As described above, the culture observation system S includes the culture observation device 1 including the culturing cabinet 2 forming the culturing environment in the culturing room 13 and the image pick-up device 3 imaging the cells (culture) cultured in the culturing cabinet 2 (in culturing room 13) and the computer 5 connected to the culture observation device 1 by a communication line. The culture observation device 1 includes the culturing cabinet-side controller C1 and an image pick-up device-side controller C2.

The cabinet temperature sensor 26, the $CO_2$ gas concentration sensor 27, the $O_2$ gas concentration sensor 28, the stage temperature sensor 46, and the control panel 16 are connected to the input side of the culturing cabinet-side controller C1 and the cabinet heater 19, the door heater 18, the stage heater 41, the $CO_2$ gas electromagnetic valve 24, the $O_2$ gas electromagnetic valve 25, and the blower motor 32 are connected to the output side thereof. A communicate line 50 for data communication with the computer 5 is connected to the culturing cabinet-side controller C1. A memory 53 is embedded in the culturing cabinet-side controller C1 to store setting values in the memory 53 on the basis of the output from the computer 5 and the output based on the operation of the control panel 16. The temperature and gas concentration of the culturing room 13 and the temperature of the table 37 are controlled on the basis of the setting values. In addition, temperature data and concentration data are output to the computer 5 by the culturing cabinet-side controller C1.

The lens 35, the CCD camera 36, the stage motors 39 and 40, the light source 47 and the like constituting the image pick-up device 3 are connected to the output side of the image pick-up device-side controller C2. A communication line 51 (composed of an image input communication line, control communication line and the like) for data communication with the computer 5 is connected to the image pick-up device-side controller C2. Accordingly, on the basis of the output from the computer 5, observation coordinate movement, illumination ON/OFF of the light source 27, luminance adjustment, control of the image taking of the CCD camera 36 are performed. In addition, coordinate position data and luminance data of the light source are output to the computer 5 by the image pick-up device-side controller C2.

The computer 5 includes an application program (a memory 9 as storage means is embedded therein) to control the culture observation device 1, input various data, and refer to and store the data and can display the various data and an obtained image (microscopic image) in the display screen of the display 4 connected thereto. Various settings can be made by the input of numeric values and the determination in accordance with the screen displayed on the display 4. A mouse 8 as operation means is connected to the computer 5.

Next, the operation of the culture observation system S according to this embodiment will be described. By operating the control panel 16 or the computer 5, culturing conditions for the culturing room 13, that is, in this embodiment, a cabinet temperature, cabinet $CO_2$ gas concentration, and $O_2$ gas concentration are set. Herein, the cabinet temperature is set to +37.0° C., the $CO_2$ gas concentration is set to 5.0%, and the $O_2$ gas concentration is set to 5.0%.

On the basis of this, the culturing cabinet-side controller C1 controls the energization of the cabinet heater 19, the door heater 18, and the stage heater 41 and maintains the temperatures of the culturing room 13 and the table 37 to a set temperature of +37.0° C. Specifically, when the cabinet temperature sensor 26 detects +36.5° C. or less, the cabinet heater 19 and the door heater 18 are energized, and when the temperature increases to +37.5° C., the cabinet heater 19 and the door heater 18 are not energized. In addition, when the stage temperature sensor 46 detects +36.5° C. or less, the stage heater 41 is energized, and when the temperature increases to +37.5° C., the stage heater 41 is not energized.

In this manner, the cabinet heater 19 and the door heater 18 controls the temperature independently of the stage heater 41. In this case, in this embodiment, the culturing cabinet-side controller C1 controls the temperature of the table 37 to a temperature lower than the temperature in the culturing room 13 and suitable for culturing cells as a culture. That is, the controller C1 controls the temperature of the table 37 to a temperature which is equal to or lower than the temperature in the culturing room 13 and higher than the temperature suitable for culturing cells (in this embodiment, +36.5° C.).

In this manner, the air temperature in the culturing room 13 can be always adjusted to be equal to or higher than the temperature of the table 37. Accordingly, a disadvantage in that dew condensation occurs on an inner surface of the sample containers 42 when the temperature of the upper part of the sample containers 42 mounted in the holes 43 of the table 37 (approximate to air temperature in culturing room 13) is lower than the temperature of the lower part of the sample containers 42 coming into contact with the table 37 (approximate to temperature of table 37) can be avoided.

Consequently, since the temperature suitable for the culturing the cells in the sample containers 42 mounted on the table 37 can be maintained and the dew condensation occurring on the inner surface of the containers can be avoided, a disadvantage in that the dew condensation obstructs the cell photographing performed via the sample container 42 can be avoided. Accordingly, the cells mounted on the table 37 can be properly observed.

Further, the culturing cabinet-side controller C1 controls the opening and closing of the $CO_2$ gas electromagnetic valve 24 and the $O_2$ gas electromagnetic valve 25 on the basis of the gas concentration ($CO_2$ gas concentration and $O_2$ gas concentration) in the culturing room 13, which is detected by the $CO_2$ gas concentration sensor 27 and the $O_2$ gas concentration sensor 28 to maintain the gas concentration in the culturing room 13 to the set gas concentration (in this embodiment, $CO_2$ gas concentration is set to 5.0% and $O_2$ gas concentration is set to 5.0%).

In this manner, the temperature and the gas concentration in the culturing room 13 can be adjusted to the set temperature and gas concentration as described above. Accordingly, by mounting the sample containers 42 containing the cells in the holes 43 of the table 37 provided in the culturing room 13, the cells can be cultured in accordance with the culturing conditions. The cells mounted on the table 37 can be observed by the image pick-up device 3 as described later in detail. In addition, in this embodiment, the plurality of shelf boards 7 are installed in the culturing room 13, and thus by mounting the containers containing the culture (cells and the like) on the shelf boards 7, the cells can be cultured in accordance with the same culturing conditions.

Accordingly, other cells (culture) other than the cells (culture) to be observed by the image pick-up device 3 also can be cultured by the same device. Thus, an accommodation amount of the cells (culture) which can be cultured at one time can be increased. Moreover, without particularly mounting a device for culturing, that is, a $CO_2$ incubator not including the image pick-up device, it is possible to perform only the culturing and perform both of the culturing state observation and the culturing simultaneously and thus convenience can be improved.

Next, the imaging (observation) of the cells (culture) cultured in accordance with the above culturing conditions will be described with reference to FIGS. 6 to 10. Since the image pick-up device 3 is controlled on the basis of the output of the computer 5, the computer program executed by the computer 5 in accordance with the display screen of the display 4 connected to the computer 5 will be described hereinbelow.

Figure 10:
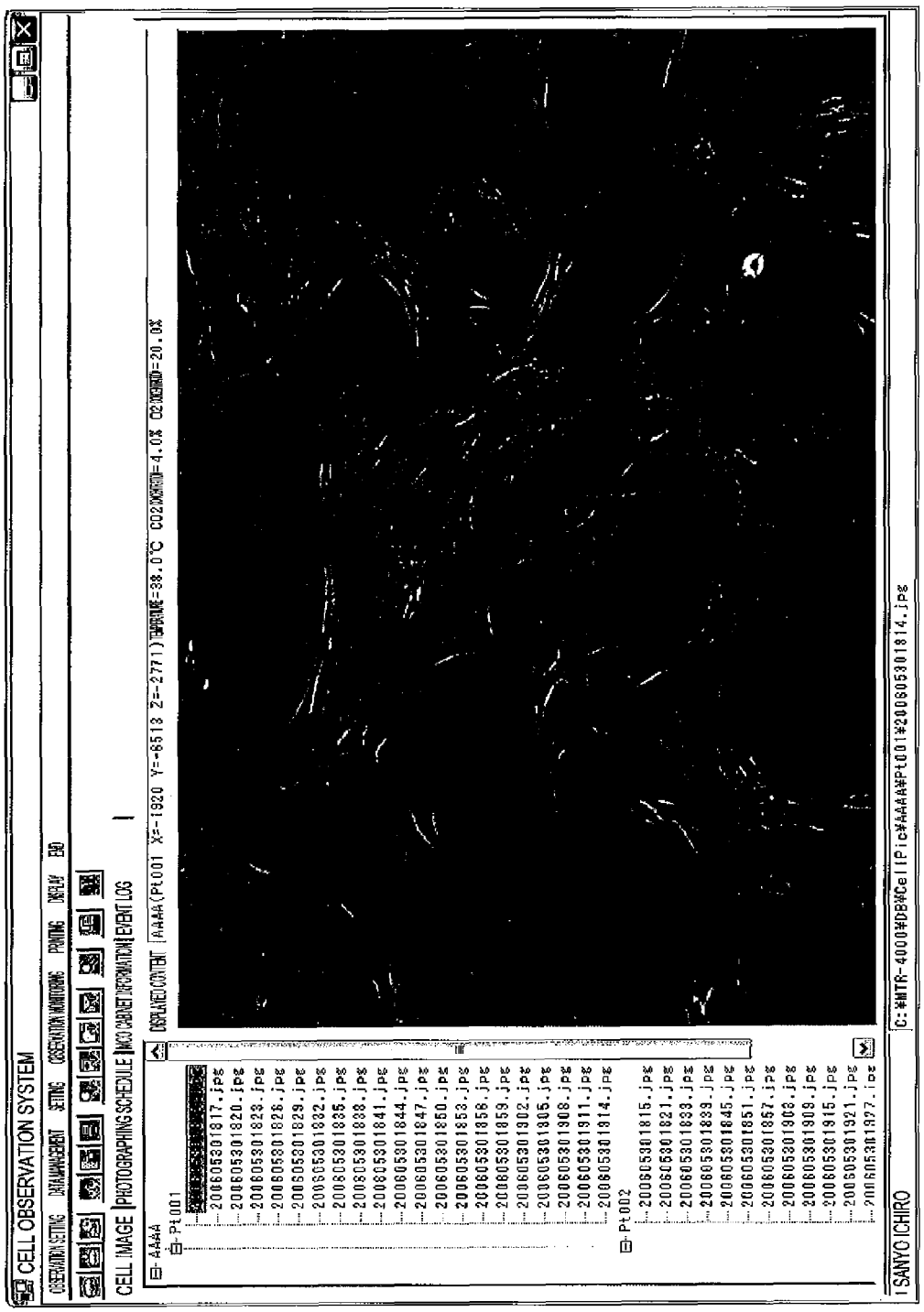
FIG. 10 is a diagram showing a "cell observation system" screen displayed on a display.

First, the computer program is started by the computer 5 to display an initial screen of "cell observation system" shown in FIG. 10 in the display screen of the display 4. "Observation setting" displayed in the initial screen of the "cell observation system" is selected and "photographing point setting" (not shown in the drawings) in the "observation setting" is selected to display "photographing point setting screen" shown in FIG. 6. In this screen, a photographing point is set. In the "photographing point setting screen", "photographing point setting", "image information of current position" "current position" and the like are displayed.

A microscopic image photographed by the current CCD camera 36 is displayed in the "image information of current position" (display in real time). A current photographing position with respect to the display of the entire table 37 is displayed in the "image information of current position". In this embodiment, an observation target which is photographed by the image pick-up device 3 is the cells in the sample containers 42 mounted in the 6 holes 43 of the table 37. As shown in the "display of current position", the table 37 has 12 stages partitioned by an angle of 30°, and a stage No., an X coordinate, a Y coordinate, and a Z coordinate are displayed as the "image information of current position" and the current photographing position is roughly displayed by "+".

Herein, the X coordinate and the Y coordinate are determined by the amount (movement amount) moved by rotating the table 37 with the stage motor 39 for rotation movement or driving the table with the stage motor 40 for linear movement, and the Z coordinate is determined by the amount (movement amount) moved by vertically moving the objective lens 44. Regarding the coordinates, an original point can be determined by operating a "stage initialization" button on the screen and the movement amount with respect to the original point is calculated. In this manner, the position which is currently photographed (movement position) is determined.

In addition, regarding the current photographing position, the photographing position can be arbitrarily moved by operating arrow buttons of "X/Y moving" and "Focus" displayed in the "photographing point setting screen". The controller C2 drives the stage motors 39 and 40 and the like on the basis of the operation of the buttons to rotate or move the table 37 in a back-and-forth direction and thus the cells on the table 37 are arbitrarily moved to a position at which the cells can be observed by the objective lens 44.

Herein, the "Focus" is a button for vertically moving the objective lens 44 at levels ranging from 0 to +5 and −5. By this, a pint of the cells as a photographing target can be arbitrarily selected. The "AF" is an auto-focus button. By operating this button, the objective lens 44 is vertically moved automatically to detect and focus on (take the focus) the Z coordinate (position) which is high in sharpness.

At this time, the computer 5 moves the objective lens 44 from a maximum value to a minimum value via the controller C2 and detects sharpness of each Z coordinate (each position). Then, the Z coordinates which are equal to or higher in sharpness than a predetermined sharpness are stored in the memory 9 together with the sharpness. At the end of the auto-focus, a microscopic image obtained by focusing on (taking the focus) the Z coordinate (position) which is the highest in sharpness is displayed in the "image information of current position".

For example, a "high AF" button and/or a "low AF" button (not shown in the drawings) are provided above and below the "AF" button. By operating the "low AF" button, an image having the next highest sharpness stored in the memory 9 is displayed in the "image information of current position" (since the image having the highest sharpness is displayed just after the end of the auto-focus operation, the image to be displayed next time becomes a microscopic image at the Z coordinate which is the second highest in sharpness).

Further, by operating the "low AF" button, an image having low sharpness stored in the memory 9 is subsequently displayed, and by operating the "high AF" button, an image having sharpness higher than that of the currently displayed microscopic image is displayed in the "image information of current position".

Figure 11:
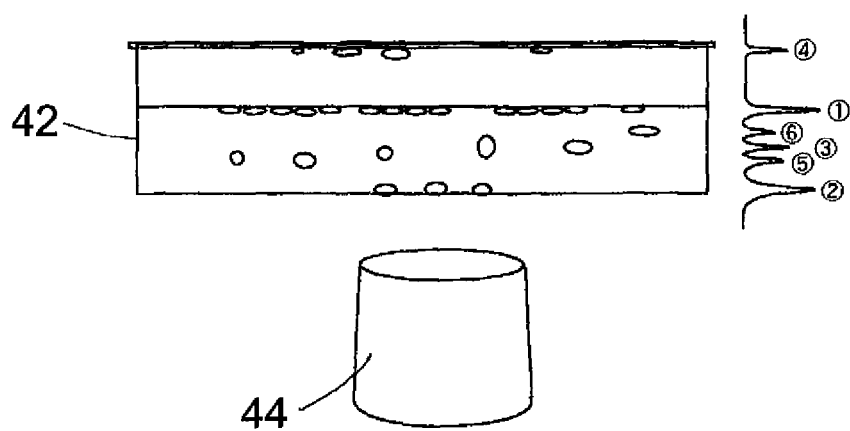
FIG. 11 is a diagram showing a relationship between a sample container and sharpness.

For example, in the sample container 42 shown in FIG. 11, water droplets and cells adhere to the lid member (inner wall of upper surface) and there are cells on the bottom surface of the container 42. In addition, there are cells on a liquid level of a culture medium or the like and cells float in the culture medium (in the liquid). When the cells in the sample container 42 are used as an observation target and the auto-focus button is operated, coordinates which are equal to or higher in sharpness than a predetermined sharpness are obtained at a plurality of points, that is, in this embodiment, at 6 points and are stored in the memory 9. Herein, a microscopic image at the Z coordinate (position) which is the highest in sharpness is obtained by observing the cells of the liquid level of the culture medium or the like and a microscopic image at the Z coordinate (position) which is the second highest in sharpness is obtained by observing the cells of the bottom surface of the container 42. Microscopic images at the Z coordinates which are the third, fifth and sixth highest in sharpness, respectively, are obtained by observing the cells floating in the culture medium and a microscopic image at the Z coordinate which is the fourth highest in sharpness is obtained by observing the water droplets and cells adhering the inner wall of the upper surface of the container 42.

Accordingly, in the "image information of current position" after the end of the auto-focus operation, the microscopic image obtained by observing the cells of the liquid level of the culture medium or the like and having the highest sharpness is displayed. Then, the microscopic image obtained by observing the cells of the bottom surface of the container 42 and having the next highest sharpness is displayed in the "image information of current position" by operating the "low AF" button. When the "low AF" button is further operated, the microscopic image having the next highest sharpness is displayed in the "image information of current position". When the "high AF" button is operated, the microscopic image having higher sharpness is displayed next to the microscopic image currently displayed in the "image information of current position".

In addition, by operating the arrow buttons of the "Focus" after the moving to the Z coordinate which is high in sharpness, the movement at levels ranging from 0 to +5 and −5 per set unit can be performed.

Accordingly, the Z coordinates which are high in sharpness with respect to a plurality of imaged planes can be automatically detected in a depth direction at the same photographing position and thus a photographing point at each Z coordinate can be easily selected. As a result, the microscopic images of a plurality of the cultures or the like at different positions in the depth direction can be easily observed.

Since not only the microscopic image having the highest sharpness obtained by the auto-focus operation but also the microscopic image having sharpness lower than that of the above microscopic image and equal to or higher than a predetermined sharpness can be directly displayed by operating the "high and low AF" buttons, the culture as an observation target can be easily photographed and thus convenience is improved.

Generally, in the microscopic image photographed at a predetermined X coordinate, the observation substance positioned on the Z coordinate plane is clearly displayed and the substance positioned deeper in the depth direction is little displayed. In addition, with the auto-focus function, it is possible to directly detect and focus on the microscopic image at the Z coordinate which is the highest in sharpness.

However, it was difficult to obtain the microscopic image having sharpness lower than that of the above microscopic image and equal to or higher than a predetermined sharpness. Accordingly, in some cases, the target cells may not be displayed in the microscopic image obtained by the auto-focus function. In this case, the auto-focus function cannot be used and the Z coordinate (position) is arbitrarily moved to search the target cells.

In this embodiment, a function of detecting a plurality of the microscopic images having sharpness equal to or higher than a predetermined sharpness and focusing on them is provided and the microscopic images can be arbitrarily displayed in the display screen of the display 4 by operating the "high AF" and "low AF" buttons. Thus, from the plurality of the microscopic images displayed by operating the "high AF" and "low AF" buttons, the observation target substance (cells) can be selected. Accordingly, the observation point setting operation is simplified.

Figure 7:
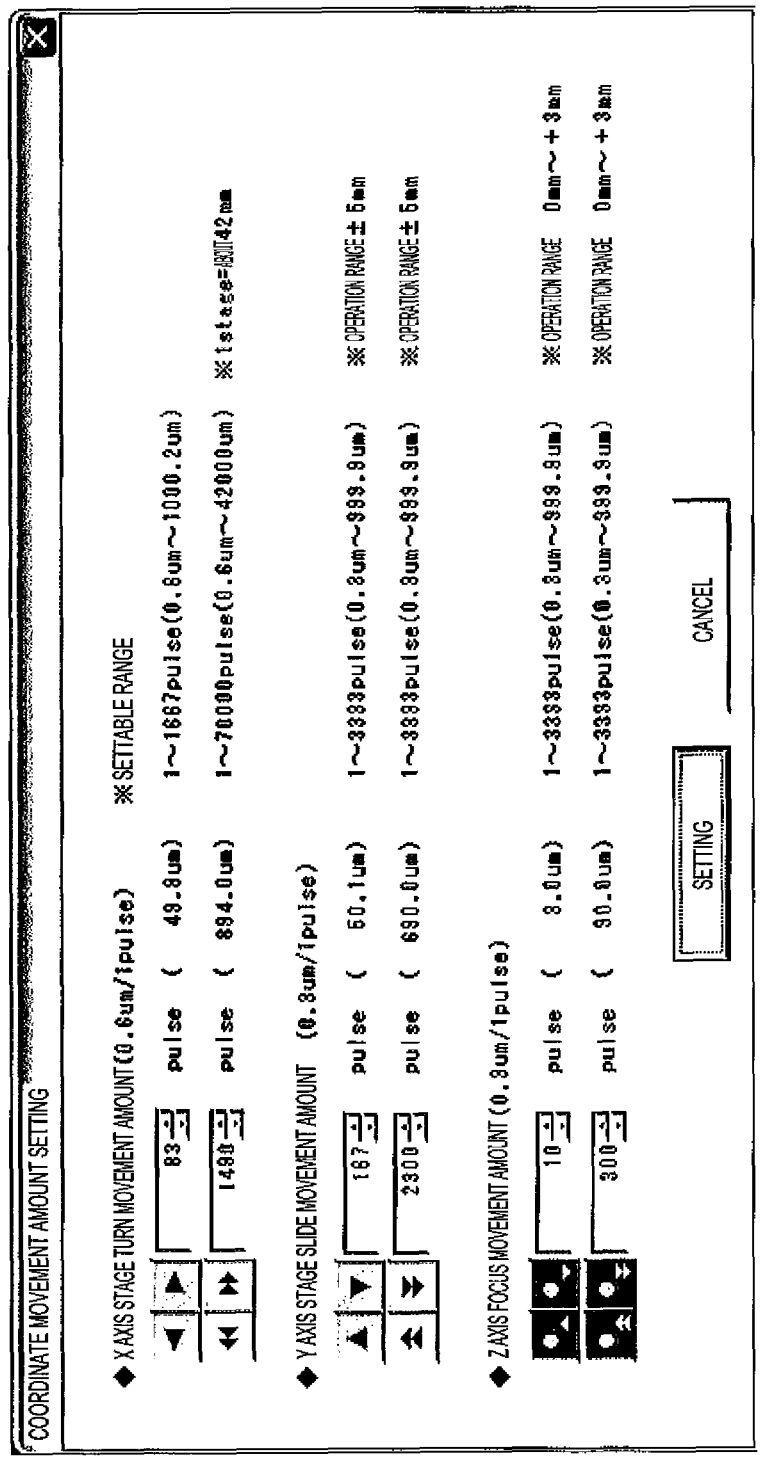
FIG. 7 is a diagram showing a "coordinate movement amount setting" screen displayed on a display.

The arrow buttons for operating the movement of the X, Y and Z axes includes both of a coarse-movement button for a relatively large movement amount and a fine-movement button for a relatively small movement amount. Regarding the coarse-movement button and the fine-movement button, a "coordinate movement amount setting screen" shown in FIG. 7 is displayed by operating a "coordinate movement amount setting" button displayed in the "photographing point setting screen", and movement amount units can be set in the screen. In the "coordinate movement amount setting screen", the setting can be made by the input of numeric values of the movement amount when the coarse-movement button and the fine-movement button of each of "X axis stage turn movement amount", "Y axis stage slide movement amount" and "Z axis focus movement amount" are operated at one time. In this embodiment, the X coordinate, the Y coordinate, and the Z coordinate are changed by the stage motors 39 and 40 and the motor for vertically moving the objective lens 44 and the motors controls the movement amount by pulse control. Accordingly, the coordinate movement can be efficiently performed in the course of the determination of the observation coordinate.

Figure 8:
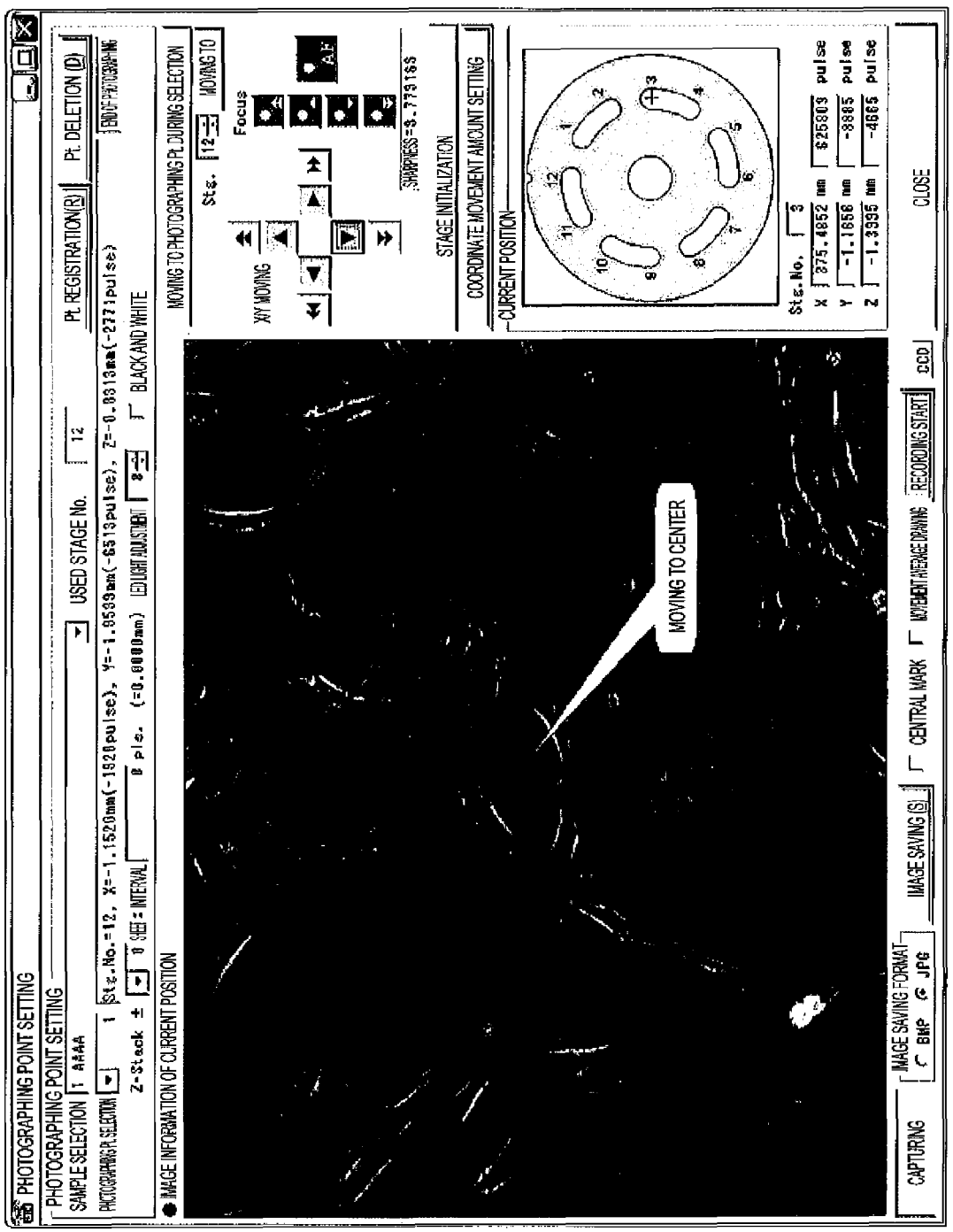
FIG. 8 is a diagram showing a "photographing point setting" screen displayed on a display.
Figure 9:
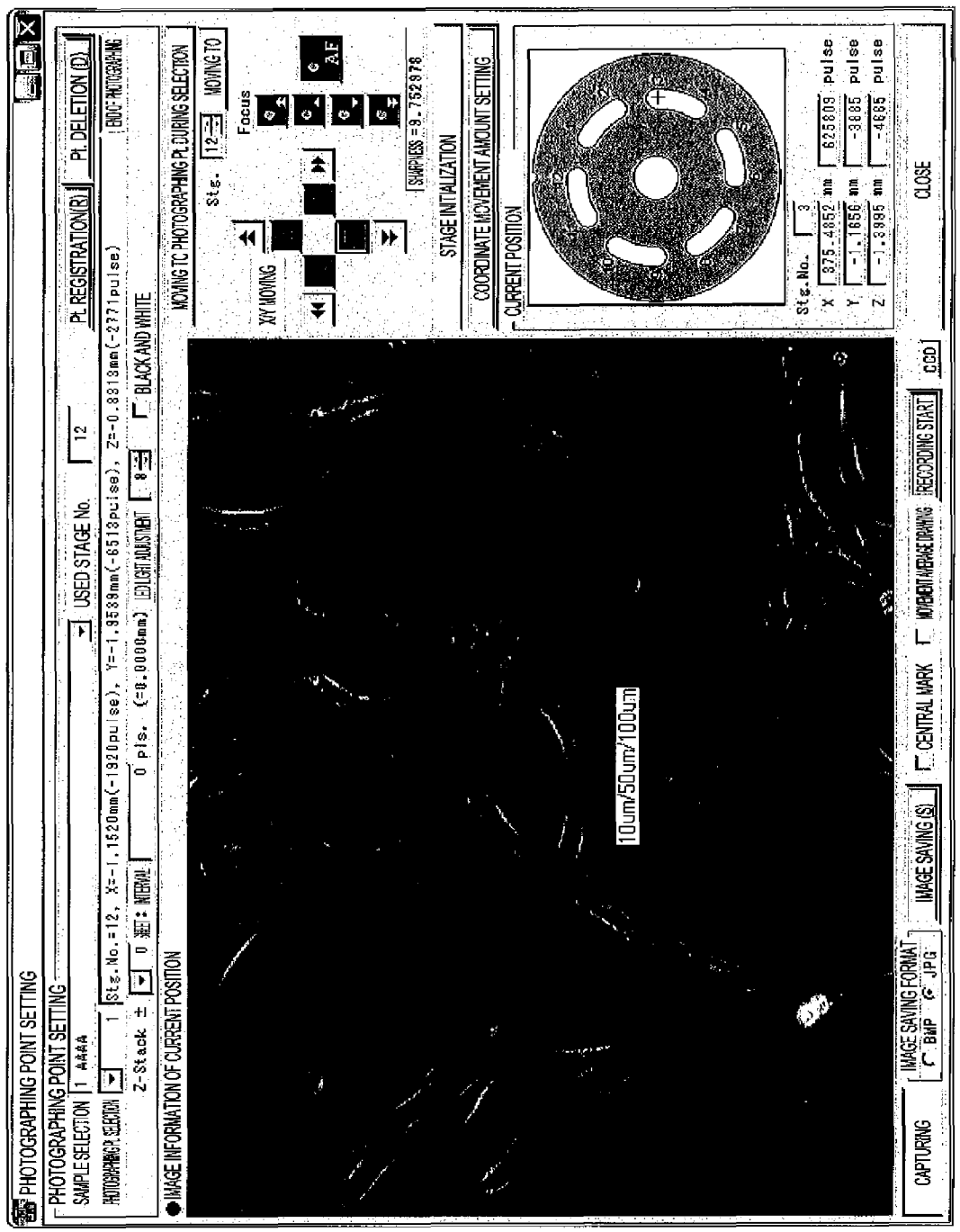
FIG. 9 is a diagram showing a "photographing point setting" screen displayed on a display.

Further, in the "photographing point setting screen", by moving a mouse cursor to an arbitrary position (arbitrary coordinate) in the "image information of current position" area and double-clicking a left button of the mouse 8 connected to the computer 5, the selected position can be moved to the center of the "image information of current position" area (state of FIG. 8). That is, the selected coordinate can be moved so as to be positioned at the center of the image display area. In this manner, the microscopic image obtained by moving the cells as an observation target to the center can be displayed in the "image information of current position" area and the observation environment can be adjusted.

Moreover, in the "photographing point setting screen", by moving the mouse cursor to the "image information of current position" area and clicking a right button of the mouse 8 one time, a cross-shaped scale is displayed (FIG. 9) for the scale display of the X and Y axes in the "photographing point setting screen" area (in microscopic image). Regarding the cross-shaped scale, tick marks having different lengths per, for example, 10 µm, 50 µm, and 100 µm (in this embodiment, the larger the scale is, the longer the tick marks are displayed) are displayed in the X and Y axes. The unit of the tick marks put on scale display is not limited to thereto. In the same screen, the tick marks may be arbitrarily changed and displayed to have different lengths per, for example, 20 µm, 100 µm, and 200 µm.

An original point (intersection point of X axis and Y axis) of the scale display can be moved around the mouse cursor position on the displayed screen by operating the mouse 8. Thus, by moving the scale display to the vicinity of arbitrary cells (certain position) displayed in the "image information of current position" area, a dimension of the cells as an observation target can be confirmed at one view. Accordingly, the approximate dimension of the cells as an observation target can be confirmed by the scale display without dependence on speculation and proper cell (cell culturing) observation can be realized.

Further, the scale display is changed by the magnification (photographing magnification) which is observed by the image pick-up device 3 and is optically changed, the size of the display screen of the display 4, and the like. Even when the display magnification is changed by digital processing of the image (microscopic image) obtained from the image pick-up device 3 in the computer 5, the tick mark unit of the scale display is changed in accordance with the size displayed in the display screen. When the display magnification increases, the size (dimension) per tick mark unit of the scale display is largely displayed, and when the display magnification decreases, the size (dimension) per tick mark unit of the scale display is displayed smaller.

Accordingly, even when the photographing magnification of the image pick-up device 3 is changed or the display magnification is changed, proper scale display can be realized and an approximate dimension of the cells as an observation target can be more properly grasped.

By clicking the right button of the mouse 8 once again, the display position of the scale display can be fixed, and by further clicking the right button once more, the scale display can be hidden (released).

In the "photographing point setting" displayed in the "photographing point setting screen", "sample selection", "used stage No.", "photographing point selection", "Z-Stack", "LED light adjustment", "black and white/color" selection are displayed.

Figure 6:
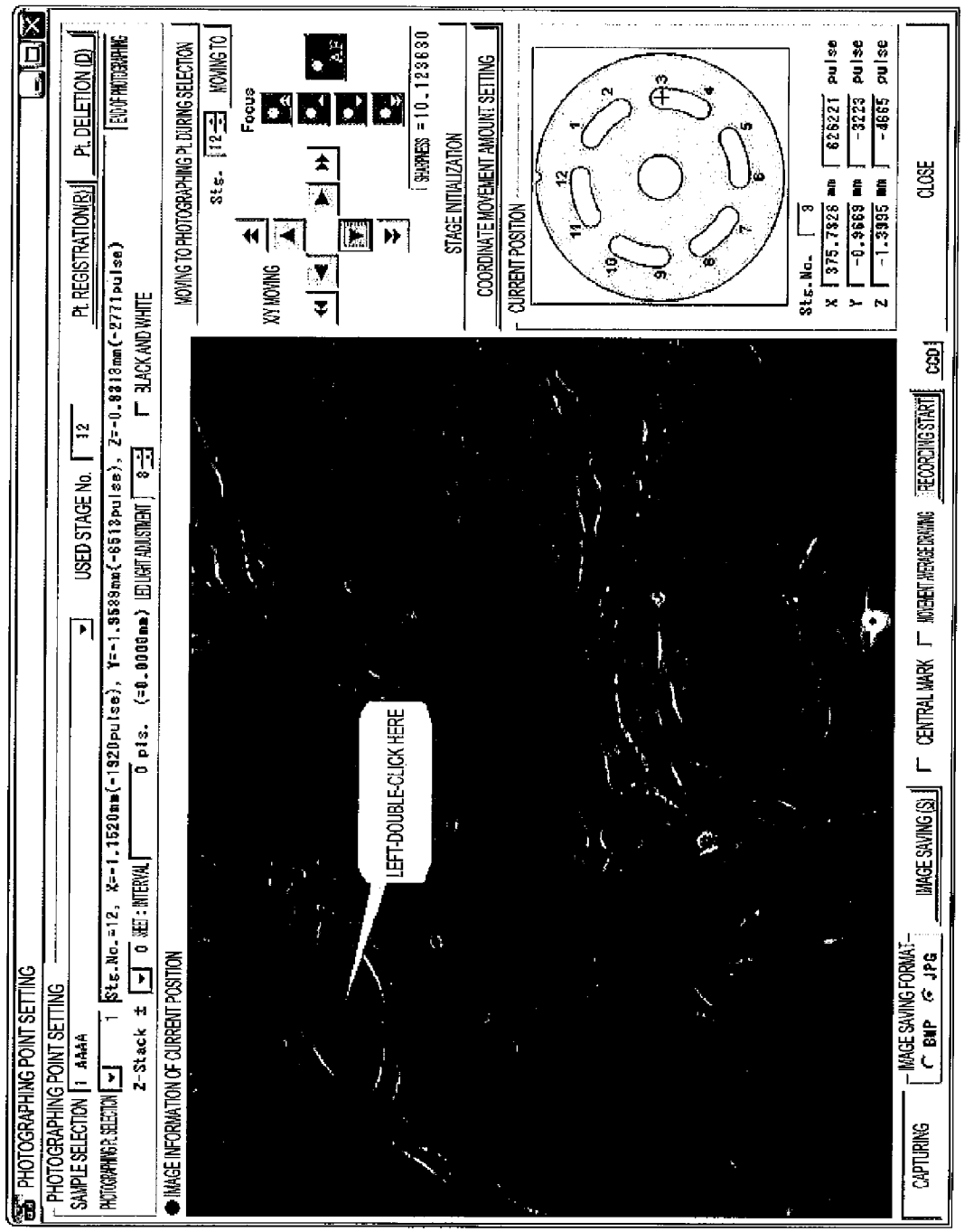
FIG. 6 is a diagram showing a "photographing point setting" screen displayed on a display.

Pre-registered sample names are displayed in the "sample selection". In the display of FIG. 6, the sample name is "1 AAA" and the used stage No. is 12. The current photographing position shown in the "image information of current position" can be registered as a photographing point and the X, Y and Z coordinates of each photographing point are displayed per registration No. in the "photographing point selection".

In the "Z-Stack", the focus (Z coordinate) with respect to each photographing coordinate (X-Y coordinate) can be registered at ±5 points per observation coordinate of time-lapse photographing to be described later in detail and the interval distance also can be set. Similarly, in the "LED light adjustment", the luminance of the LED as the light source 47 can be set per observation coordinate of the time-lapse photographing. In addition, black and white photographing mode or color photographing mode can be set per observation coordinate of the time-lapse photographing by selecting or not selecting the "black and white".

Further, the stage No. can be designated and the moving to the stage base point can be performed. In addition, the direct moving to the preset photographing point also can be performed by operating a "moving to photographing Pt. during selection". The X, Y and Z coordinates of the photographing point after being elected are displayed in detail in the "photographing point setting".

As described above, when the photographing point is set in the "photographing point setting screen" and then the setting screen is closed, the computer 5 displays the "cell observation system" screen on the display 4. The "observation setting"

displayed in the cell observation system" screen is selected and "observation condition" (not shown in the drawings) in the "observation setting" is selected to display "observation condition input screen" (not shown in the drawings), and in the "observation condition input screen", a photographing condition is input to perform the time-lapse observation.

The time-lapse photographing is a function of automatically performing photographing at a predetermined time interval and recording the photographed microscopic image in the memory 9 of the computer 5 and is suitable for the observation of change of living cells with the lapse of time.

In the "observation condition input screen", a plurality of or one photographing time can be set per "photographing point" set in the "photographing point setting screen". In photographing using the time-lapse function, particularly, in multipoint time-lapse photographing in which a plurality of photographing points are simultaneously set, the setting is performed in consideration of the time-lapse interval time since it may affect the stage movement (movement of table 3) time after the photographing, photographing time, and exposure time.

When the photographing condition is set in the "observation condition input screen" and then the setting screen is closed, the computer 5 displays the "cell observation system" screen. In accordance with the set photographing condition, the computer 5 is controlled and thus the photographing is performed at the set photographing point at the set photographing time.

The computer 5 stores, in the memory 9, the photographed microscopic image in association with a photographing date (photographing time) and culturing environment information such as the temperature data (cabinet temperature, stage temperature) and gas concentration data ($CO_2$ gas concentration, $O_2$ gas concentration) output from the culturing cabinet-side controller C1 at the photographing time.

In "cell image sheet" of the "cell observation system", the microscopic image stored in the memory 9 is displayed in association with the photographing date and the culturing condition information. Accordingly, in the time-lapse photographing, the photographed microscopic image can be displayed together with the culturing condition information, and thus the culture information corresponding to the microscopic image can be properly confirmed and reliability can be improved as observation data.

In the display of the microscopic image of the "cell observation system" screen, the scale display also can be performed as in case of the display of the "image information of current information" of the "photographing point setting screen". Accordingly, even in a stored microscopic image, a dimension of cells as an observation target can be confirmed by the scale display without dependence on speculation and proper cell (cell culturing) observation can be realized.

What is claimed is:

1. A culture observation system comprising:
   a culturing cabinet having therein a culturing room for forming an environment suitable for culturing a culture; and
   an image pick-up device for photographing a microscopic image of the culture,
   wherein the image pick-up device includes a table which is provided in the culturing room to hold the culture as an image pick-up target accommodated in a translucent container,
   wherein a cabinet heater for heating the culturing room, a stage heater for heating the table, a cabinet temperature sensor for detecting a temperature in the culturing room and a stage temperature sensor for detecting a temperature of the table are provided, and
   wherein control means for controlling the temperature in the culturing room and the temperature of the table is provided and controls the temperature in the culturing room and the temperature of the table by controlling the cabinet heater and the stage heater independently based on a detecting value of the cabinet temperature sensor and the stage temperature sensor so that the temperature of the table to be a value equal to or lower than the temperature in the culturing room.

2. A culture observation system according to claim 1, wherein:
   the translucent container is held on the table in a state in which the lower part of the translucent container comes into contact with the table.

* * * * *